United States Patent
Chen et al.

(10) Patent No.: US 11,399,864 B2
(45) Date of Patent: Aug. 2, 2022

(54) HANDLE ASSEMBLY AND STAPLER INCLUDING THE SAME

(71) Applicant: TOUCHSTONE INTERNATIONAL MEDICAL SCIENCE CO., LTD., Jiangsu (CN)

(72) Inventors: Zhi Chen, Jiangsu (CN); Yi Guo, Jiangsu (CN); Jiang Lin, Jiangsu (CN); Xiaowei Xu, Jiangsu (CN)

(73) Assignee: TOUCHSTONE INTERNATIONAL MEDICAL SCIENCE CO., LTD.

( * ) Notice: Subject to any disclaimer, the term of this patent is extended or adjusted under 35 U.S.C. 154(b) by 168 days.

(21) Appl. No.: 16/957,580

(22) PCT Filed: Dec. 19, 2018

(86) PCT No.: PCT/CN2018/122049
§ 371 (c)(1),
(2) Date: Jun. 24, 2020

(87) PCT Pub. No.: WO2019/128798
PCT Pub. Date: Jul. 4, 2019

(65) Prior Publication Data
US 2020/0330119 A1    Oct. 22, 2020

(30) Foreign Application Priority Data

Dec. 26, 2017   (CN) .......................... 201711434086.9
Dec. 26, 2017   (CN) .......................... 201721846936.1

(51) Int. Cl.
*A61B 17/064* (2006.01)
*A61B 17/326* (2006.01)
*A61B 17/00* (2006.01)

(52) U.S. Cl.
CPC .. *A61B 17/326* (2013.01); *A61B 2017/00367* (2013.01)

(58) Field of Classification Search
CPC ...... A61B 17/1155; A61B 2017/00367; A61B 2017/2925
See application file for complete search history.

(56) References Cited

U.S. PATENT DOCUMENTS 3,480,087 A * 11/1969 Boeger ................. B25B 23/145
                                                           91/1
3,858,444 A *  1/1975 Wallace ............. B25B 23/1456
                                                        73/862.21
(Continued)

FOREIGN PATENT DOCUMENTS

CN       201098164 Y    8/2008
CN       105310747 A    2/2016
(Continued)

OTHER PUBLICATIONS

Extended European Search Report regarding corresponding AP App. No. 18896785.5; dated Sep. 10, 2021.
(Continued)

*Primary Examiner* — Eyamindae C Jallow
(74) *Attorney, Agent, or Firm* — Dickinson Wright PLLC

(57) ABSTRACT

A handle assembly and a stapler including the same are provided. The handle assembly includes: an indicator; a first handle and a second handle; a slot and a slider, provided in the first handle, the slider can be actuated by the indicator to move from a first section to a second section of the slot; when the slider in in the first section, the second handle cannot be actuated by the first handle and is in an insurance position; when the slider is in the second section of the slider, and the second handle can be actuated by the first handle to move towards a firing position. Therefore, no matter whether the stapler is ready to be fired or not, the first handle can be pressed by the doctor. However, when the stapler is not ready to be fired, the second handle won't be actuated to fire the stapler.

15 Claims, 21 Drawing Sheets

(56) References Cited

U.S. PATENT DOCUMENTS

| | | | | |
|---|---|---|---|---|
| 4,016,941 A * | 4/1977 | Sanders | ............... | B23D 29/00 |
| | | | | 403/322.2 |
| 4,591,085 A * | 5/1986 | Di Giovanni | ........ | A61B 17/072 |
| | | | | 227/19 |
| 5,376,098 A | 12/1994 | Fontayne et al. | | |
| 7,770,775 B2 * | 8/2010 | Shelton, IV | ..... | A61B 17/07207 |
| | | | | 227/176.1 |
| 9,463,556 B2 * | 10/2016 | Lefavour | ................ | B25B 17/00 |
| 9,603,599 B2 * | 3/2017 | Miller | ................ | A61B 17/1155 |
| 2009/0206123 A1 | 8/2009 | Doll et al. | | |
| 2010/0051669 A1 | 3/2010 | Milliman | | |
| 2010/0059571 A1 | 3/2010 | Chen et al. | | |
| 2013/0240228 A1* | 9/2013 | Lefavour | ................ | B25B 17/00 |
| | | | | 173/20 |
| 2015/0217422 A1* | 8/2015 | Esenwein | ................ | B25F 5/00 |
| | | | | 173/217 |

FOREIGN PATENT DOCUMENTS

| | | |
|---|---|---|
| CN | 106388948 A | 2/2017 |
| CN | 206261635 U | 6/2017 |
| CN | 1969768 A | 8/2017 |
| CN | 106994034 A | 8/2017 |
| JP | S6148345 A | 3/1986 |
| JP | 61-048345 U | 4/1986 |
| JP | H05212041 A | 8/1993 |
| JP | 3148464 U | 2/2009 |
| JP | 2009189831 A | 8/2009 |
| JP | 2015503949 A | 2/2015 |
| JP | 2017099988 A | 6/2017 |
| RU | 145252 U1 | 9/2014 |

OTHER PUBLICATIONS

First Office Action regarding corresponding JP App. No. 2020-534896; dated Jun. 24, 2021.

International Search Report regarding related PCT App. No. PCT/CN2018/122049; dated Mar. 6, 2019.

First Office Action regarding corresponding JP App. No. 2020-534896; dated Jun. 29, 2021.

Communication regarding related RU App. No. 2020122623/1 issued Nov. 13, 2020.

* cited by examiner

HANDLE ASSEMBLY AND STAPLER INCLUDING THE SAME

CROSS-REFERENCE TO RELATED APPLICATIONS

This application is based upon PCT patent application No. PCT/CN2018/122049, filed on Dec. 19, 2018, which claims priority to Chinese Patent Applications No. 201711434086.9 and No. 201721846936.1, filed on Dec. 26, 2017, the entire contents of incorporated herein by reference.

TECHNICAL FIELD

The present disclosure relates to medical instruments' technology, more particularly, to stapler technology, and specifically to a handle assembly and a stapler including the same.

BACKGROUND

Digestive tract tumor is one of human diseases of high incidence. During treatment a circular stapler is widely used for suturing physiological tissues such as tissues in the digestive tract, instead of the manual operation by doctors. The circular stapler is a common surgical instrument, and used for suturing from end to end, or from end to side of the physiological tissues of esophagus, stomach, intestine, etc., in a way of axial internal stapling. During the process of anastomoses, two sections of tissues are accommodated in the stapler, and form a circular anastomotic stoma after firing the stapler, to rebuild a tissue channel.

In the prior art, the circular stapler includes an instrument body, a handle assembly movably connected to the instrument body and an anvil assembly cooperated with the instrument body. The instrument body includes a cartridge assembly located on a distal end and a knob located on a proximal end thereof. The cartridge assembly includes a circular cartridge and a cutter, and the knob can be rotated relative to the instrument body. In the present disclosure, the positions of the distal end and the proximal end are defined relative to an operator, wherein, the proximal end is an end closer to the operator, the distal end is another end far from the operator and closer to a surgical position. The anvil assembly includes an anvil, an anvil cap on the top of the anvil, a cutter anvil inside the anvil and an anvil shaft detachably connected to the instrument body. During operation, after the tumor tissues are separated and removed, the anvil shaft is connected to the distal end of instrument body through a purse on one end of the tissues, the knob is rotated to shorten a distance between the cartridge and the anvil to an appropriate distance. The stapler is then able to be fired by pressing the handle to accomplish the suturing operation. Along with the development of medical instruments, the circular stapler has been more and more widely used for treatment of diseases such as hemorrhoids.

Meanwhile, in urinary surgical field, another kind of circular stapler is also applied to treat redundant prepuce and phimosis, which is called circumcision stapler. The structure of the circumcision stapler is similar to the circular stapler for digestive tract as aforementioned, except for the glans cap assembly cooperated with the instrument body. Similarly, the glans cap assembly includes an anvil, a glans cap fixedly connected to the anvil, a cutter anvil and a central rod detachably connected to the instrument body. During operation, the prepuce tissues to be cut are fixed to the glans cap, the central rod is configured to the distal end of the instrument body, and the knob is rotated to shorten a distance between the glans gap and the cartridge to an appropriate distance. The stapler is then able to be fired by pressing the handle to accomplish the anastomosis.

Along with the technological development, the firing transmission mechanism of the circular stapler has been improved with a lockout mechanism added. Therefore, when the stapler is not ready to be fired, even the doctor presses the handle, the handle cannot be moved for the lockout mechanism, to prevent the stapler from being fired by mistake. However, in practice, the lockout mechanism has some defects. For example, the lockout mechanism has some negative impacts on the operators' experience, and the casing of the stapler may be cracked if the doctor presses the handle vigorously.

SUMMARY

In the light of the problems in the prior art, the object of the present disclosure is to provide a handle assembly and a stapler including the same, to realize that, the first handle can be pressed by the doctor to move no matter whether the stapler is ready to be fired or not, while, the stapler cannot be fired by the first handle through the second handle when the stapler is not ready to be fired, and to prevent the casing from being cracked by pressing the handle vigorously.

In the present disclosure, a handle assembly for firing a stapler is provided, including: an indicator, movable between a first position area and a second position area; a first handle and a second handle; a slot, provided in the first handle and including a first section and a second section connected with each other; and a slider, slidably located in the slot; wherein, when the indicator is moved from the first position area to the second position area, the slider is actuated to move from the first section to the second section of the slot; when the slider is in the first section of the slot, and the first handle is rotated in a first direction, the slider is not in contact with the second handle, therefore, the second handle is in an insurance position; when the slider is in the second section of the slot, and the first handle is rotated in the first direction, the slider is in contact with the second handle and actuates the second handle to move from the insurance position to a firing position.

In some embodiments, the indicator is connected to a distal end of a pulling sheet, a proximal end of the pulling sheet is sleeved on a screw rod having a proximal end connected to a knob, when the knob is rotated to pull the pulling sheet to move towards the proximal end thereof, the indicator is moved by the pulling sheet from the first position area to the second position area.

In some embodiments, the first handle is rotatably connected to the second handle through a first pin, the second handle is rotatably connected to a casing of the stapler through a second pin.

In some embodiments, a first torsion spring and a second torsion spring are sleeved on the first pin and the second pin, respectively, two ends of the first torsion spring are in contact with the first handle and the second handle, respectively, two ends of the second torsion spring are in contact with the second handle and the casing of the stapler, respectively.

In some embodiments, the stapler further includes a return spring for the slider, after the return spring is forced by the slider to be in a deformation state, the return spring restores from the deformation state to its initial state, thereby actuating the slider to move from the second section to the first section of the slot.

In some embodiments, the return spring is a return torsion spring, two ends of the return torsion spring are in contact with the slider and the second handle, respectively.

In some embodiments, the second handle includes a handle guiding portion, the slider includes a sliding portion movably located in the slot and a slider guiding portion; when the slider is in the second section of the slot, and the first handle is rotated in a first direction, the slider guiding portion is in contact with the handle guiding portion.

In some embodiments, the handle guiding portion includes a first handle guiding surface and a second handle guiding surface adjacent to each other, the slider guiding portion includes a guiding section having a first slider guiding surface and a second slider guiding surface adjacent to each other; when the slider guiding portion is in contact with the handle guiding portion, the positions of the second slider guiding surface and the second handle guiding surface are in corresponding and parallel to each other.

In some embodiments, an angle between the second handle guiding surface and a length direction of the slot is less than 90°.

In some embodiments, when the second slider guiding surface is in contact with the second handle guiding surface, and when the first handle is rotated in the first direction, a force F is applied to the second handle guiding surface by the second slider guiding surface, the force F includes two components F1 and F2 perpendicular to each other, the component F1 is perpendicular to the second slider guiding surface, and $F1 \times \beta < F2$, wherein, $\beta$ is a friction coefficient between the second slider guiding surface and the second handle guiding surface.

In some embodiments, the slider guiding portion further includes a connecting section adjacent to the guiding section, the connecting section includes a third slider guiding surface adjacent to the second slider guiding surface.

In some embodiments, the first handle includes a first cavity having two side walls, two slots are provided on the two side walls of the first cavity, respectively, the slider includes two sliding portions and the slider guiding portion, the two sliding portions are movably located in the slot; when the two sliding portions are in the first sections of the two slots, respectively, and the first handle is rotated in the first direction, the second handle at least partially gets into the first cavity; when the sliding portions are in the second sections of the two slots, respectively, and the first handle is rotated in the first direction, the slider guiding portion is in contact with the second handle to prevent the second handle from continuing to get into the first cavity.

In some embodiments, the second handle includes a second cavity having two side walls, the handle guiding portion is in the second cavity, and a width of the handle guiding portion is less than or equal to that of the slider guiding portion.

In some embodiments, the slider further includes a boss located between one of the sliding portions and the slider guiding portion, a concave portion is provided on the top of the boss, and a return spring for the slider is provided between an inner surface of the concave portion and the second handle.

In the present disclosure, a stapler is provided including the handle assembly as aforementioned.

The handle assembly and the stapler including the same has the following advantages.

In the present disclosure, the handle assembly includes a first handle and a second handle, and only the movement of the second handle can fire the stapler to cut and suture tissues; during operation, the first handle can be pressed by the doctor to move no matter whether the stapler is ready to be fired or not, while, the stapler cannot be fired by the first handle through the second handle when the stapler is not ready to be fired. The doctor can judge whether the stapler is ready to be fired or not according to his operation experience. The stapler can only be fired by the first handle through the second handle when the stapler is ready to be fired. The casing can be prevented from being cracked by pressing the handle vigorously, and the operators' experience is improved.

BRIEF DESCRIPTION OF THE DRAWINGS

Embodiments of the present disclosure will now be described, by way of example only, with reference to the accompanying schematic drawings, and the other technical features, objects and advantages will be more obvious.

DETAILED DESCRIPTION

In the following, embodiments of the present disclosure will be described in detail with reference to the figures. The concept of the present disclosure can be implemented in a plurality of forms, and should not be understood to be limited to the embodiments described hereafter. In contrary, these embodiments are provided to make the present disclosure more comprehensive and understandable, and so the conception of the embodiments can be conveyed to those skilled in the art fully. Same reference signs in the figures refer to same or similar elements, so repeated description of them will be omitted.

Figure 1:
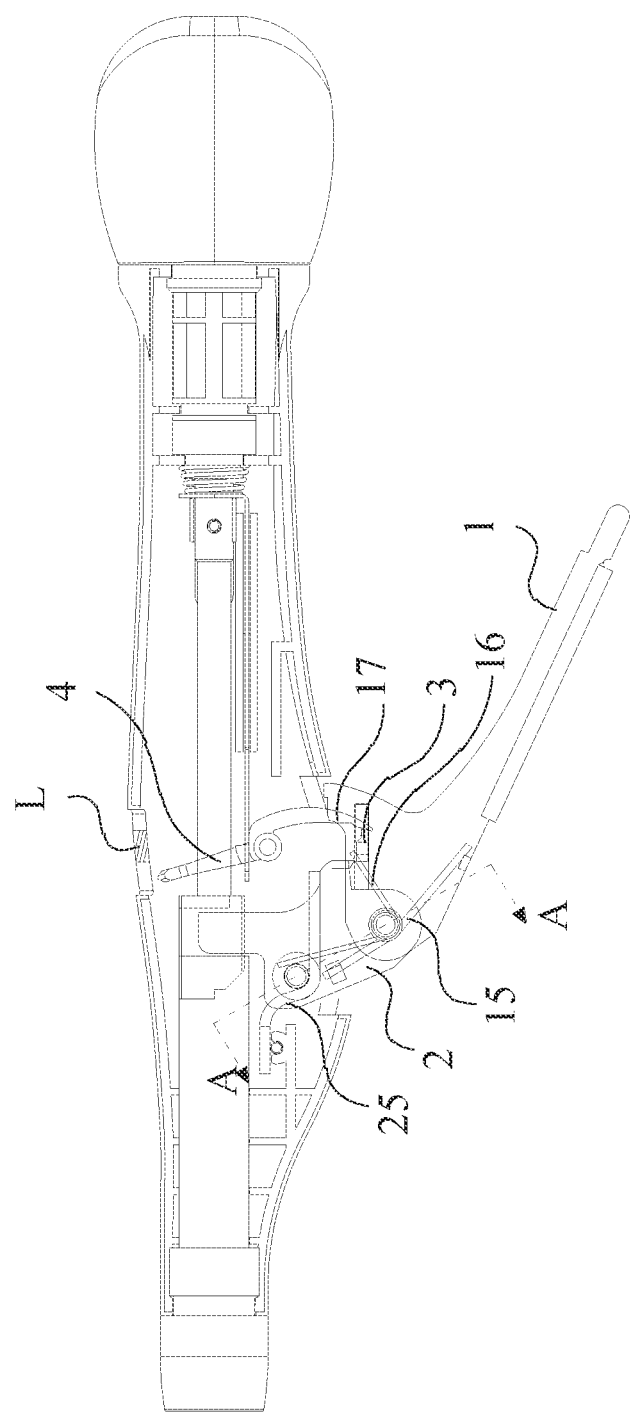
FIG. 1 is a schematic view of a handle assembly used in a stapler according to an embodiment of the present disclosure.

As shown in FIG. 1, to realize the object as aforementioned, a handle assembly for firing a stapler is provided according to an embodiment of the present disclosure. In the embodiment, the handle assembly is divided into a first handle 1 and a second handle 2 (in FIG. 1, a casing of the handle assembly is omitted for clear presentation), and only the rotation of the second handle 2 can fire the stapler. The handle assembly further includes an indicator to control the relative movement between the first handle 1 and the second handle 2.

The indicator 4 includes a first end 41, a second end 42 and a fixed end. The second end 42 of the indicator 4 is connected to a distal end of a pulling sheet having a proximal end sleeved on a screw rod and a proximal end of the screw rod is connected to a knob. The knob can be rotated to actuate the second end 42 of the indicator to move between a first position area and a second position area through the pulling sheet. Wherein, a window is provided on the instrument body, between the first position area and the second position area, through which the position of the second end 42 of the indicator can be observed during operation. When the second end 42 of the indicator is in the first position area, the stapler is in an insurance state and not ready to be fired. When the second end 42 of the indicator is in the second position area, the stapler is ready to be fired. To give a more obvious indication to the doctor, the second position area L indicating the stapler being ready to be fired is colored green, which is already existed in the prior art.

A slot 17 and a slider 13 are provided on the first handle. The slot 17 includes a first section and a second section connected to each other, and the slider 13 is movably located in the slot 17. When the second end 42 of the indicator 4 is moved from the first position area to the second position area, the slider 3 is actuated to move from the first section to the second section of the slot 17. The indicator 4 actuating the slider 3 here, refers to the indicator 4 pushing (or pulling) the slider 3 directly or indirectly. For example, a transmission rod or another kind of transmission mechanism can be provided between the indicator 4 and the slider 3, to transmit the movement of the indicator 4 to the slider 3, which is within the scope of the present disclosure.

When the slider 3 is in the first section of the slot 17, and the first handle 1 is pressed to rotate in a first direction, the slider 3 is not in contact with the second handle 2, and the second handle 2 is in an insurance position. When the slider 3 is in the second section of the slot 17, and the slot 17 is rotated along with the first handle 1 in a first direction, the slider 3 is in contact with the second handle 2 and actuates the second handle 2 to move from the insurance position to a firing position. In the embodiment, the first direction is an anticlockwise direction shown in the FIG. 1 and a moving direction of the first handle when pressed.

When the second end 42 of the indicator 4 is in the first position area and the second area, the movement of the first handle 1 has different effects on the second handle 2. When the second end 42 of the indicator 4 is in the first position area, and the slider 3 is in the first section of the slot 17, the slider 3 during movement is not in contact with the second handle 2, therefore the second handle 2 won't be actuated by the slider 3, and still stays in its initial insurance state, and the stapler cannot be fired. When the indicator 4 is in the second position area and the slider 3 is in the second section of the slot 17, during the process of the first handle being pressed to move anticlockwise, the second handle 2 is actuated by the slider 3 to move to the firing position. Therefore, the cooperation relationship between the first handle 1 and the second handle 2 can be controlled by changing the position of the indicator 4.

In summary, when the stapler is not ready to be fired, the second end 42 is in a first position area. At this time, the first handle 1 can be rotated easily when pressed by the doctor, while the second handle 2 will not be actuated. Therefore, the stapler is in an invalid firing state, and the first handle can be rotated by a very small force. The doctor can also know the stapler is in the invalid firing state through the operation experience and the casing of the stapler will not be cracked. When the stapler is ready to be fired, the indicator 4 is in the second position area. At this time, when the doctor presses the first handle 1, the first handle 1 will actuate the second handle 2 to move, thereby firing the stapler.

It should be noted that, the first and the second sections of the slider 17 are relative definitions, that is to say, the first section is on the right side of the second section of the slot 17 shown in FIG. 1.

Figure 2:
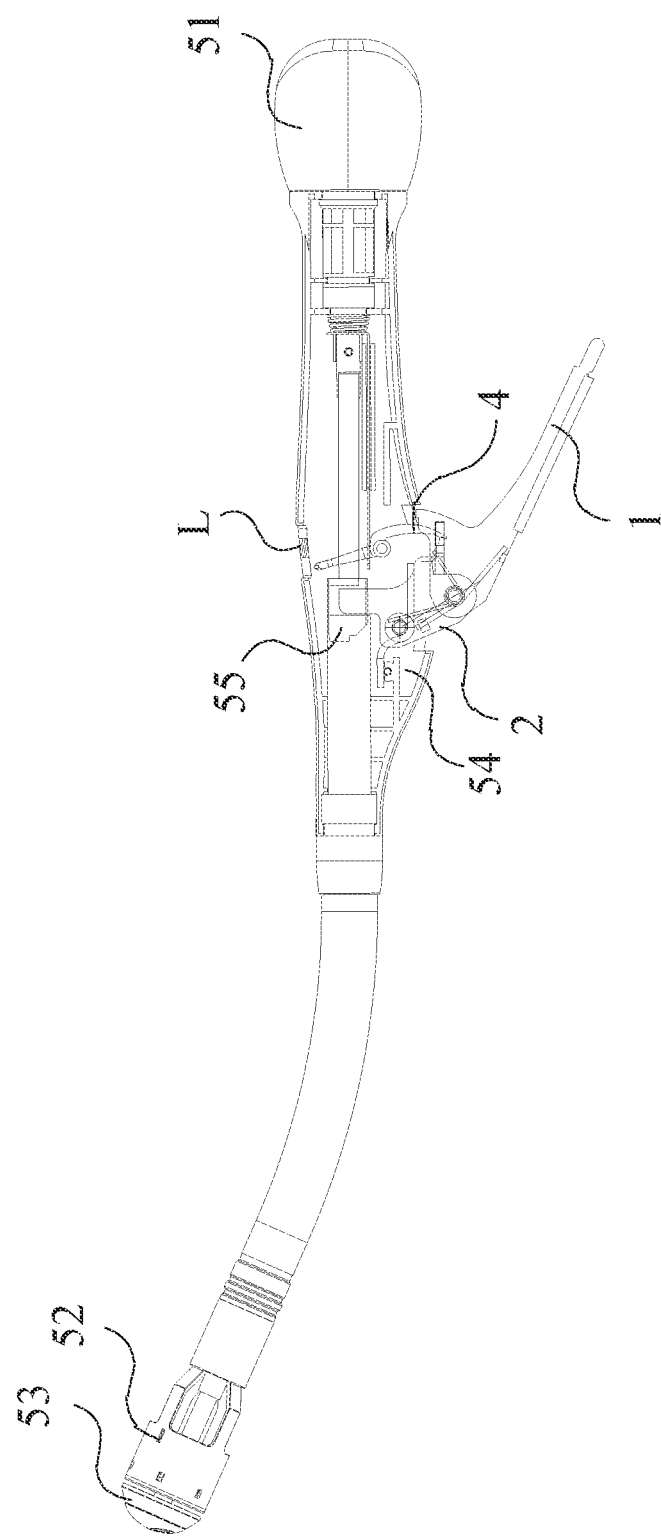
FIG. 2 is a schematic view of a circular stapler according to the embodiment of the present disclosure.
Figure 3:
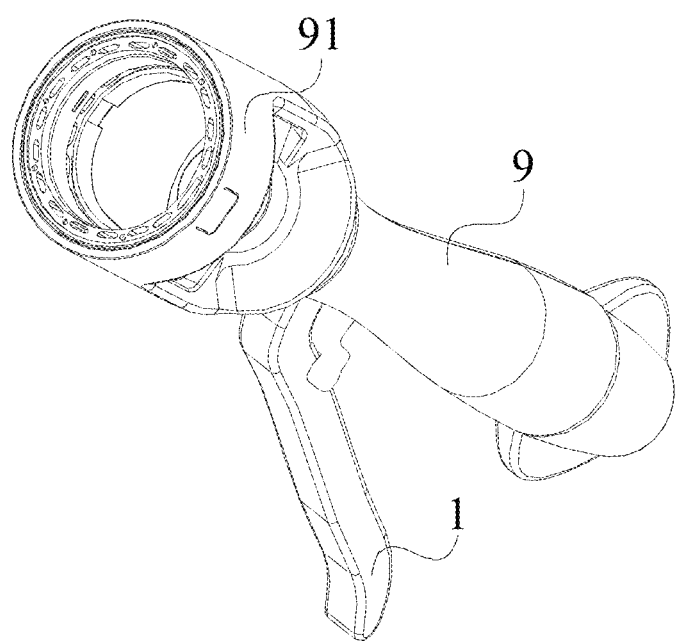
FIG. 3 is a schematic view of the handle assembly used for a circumcision stapler according to the embodiment of the present disclosure.

FIG. 2 is a schematic view of the handle assembly used in a stapler according to the embodiment of the present disclosure, and a circular stapler is shown therein. One end of the stapler includes a cartridge assembly 52 and an anvil assembly 53, the other end of the stapler includes a knob 51 and the handle assembly, and a second end of the second handle 2 is cooperated with a proximal end of a staple pushing rod 55. When the stapler is ready to be fired, the staple pushing rod 55 is pushed by the second handle to push a staple pushing sheet and a circular cutter of the stapler, thereby cutting and suturing the tissues to be operated. FIG. 2 only shows the structure of the stapler as an example, in other embodiments, the handle assembly can also be used in other kinds of staplers to realize the object of the present disclosure. For example, FIG. 3 is a schematic view of an instrument body 9 of a circumcision stapler including the handle assembly. The instrument body 9 of the circumcision stapler includes a cartridge assembly 91, and a glans cap (not shown in the FIGS) cooperated with the cartridge assembly 91. The second handle 2 is movably connected to one end of the circumcision stapler, the second end of the second handle 2 is cooperated with the staple pushing component of the circumcision stapler. When the stapler is ready to be fired, the staple pushing component is pushed by the second handle 2 to fire the circumcision stapler.

Figure 4:
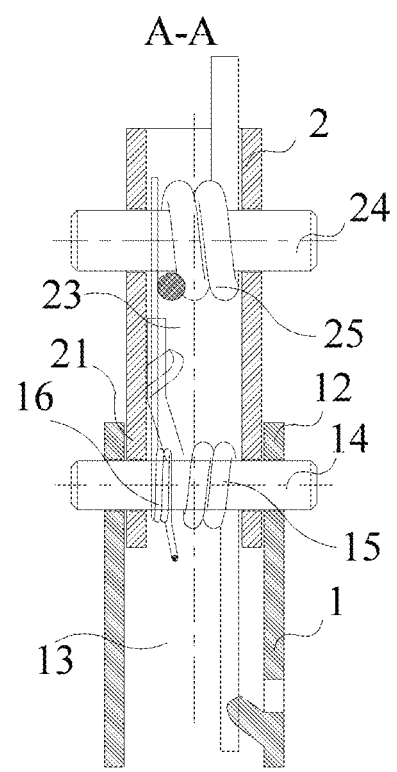
FIG. 4 is a section view along A-A direction of FIG. 1.
Figure 5:
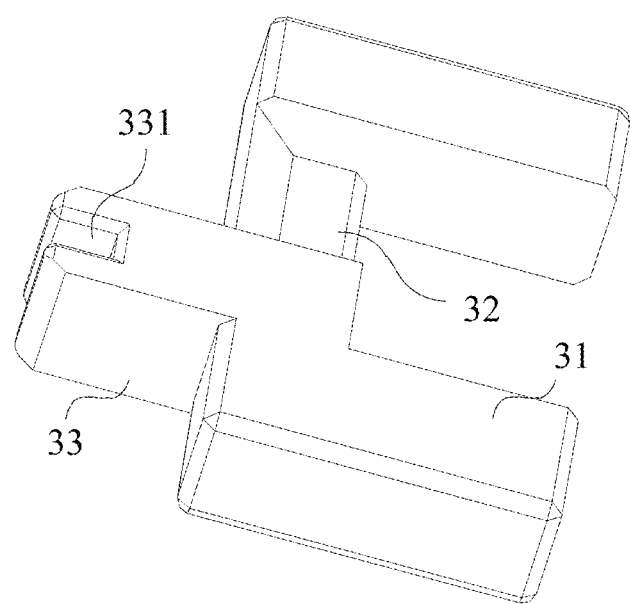
FIG. 5 is a schematic view of a slider according to the embodiment of the present disclosure.
Figure 6:
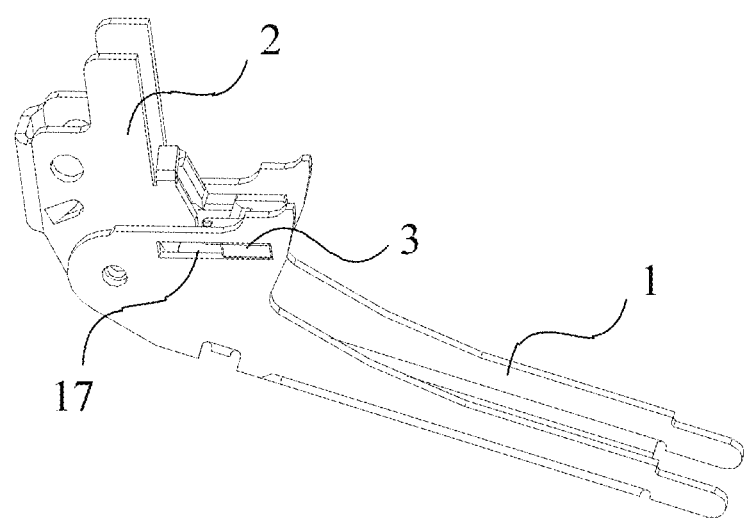
FIG. 6 is a schematic view of the handle assembly when the slider is in a first section of a slot, according to the embodiment of the present disclosure.
Figure 7:
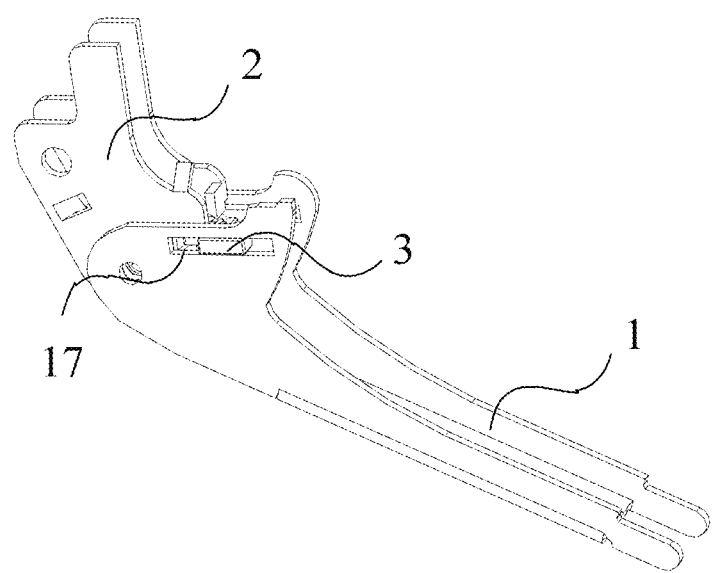
FIG. 7 is a schematic view of the handle assembly when the slider is in a second section of the slot, according to the embodiment of the present disclosure.
Figure 8:
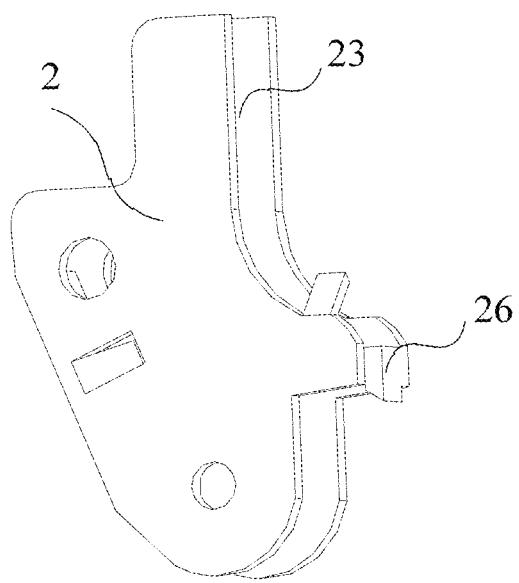
FIG. 8 is a schematic view of a second handle according to the embodiment of the present disclosure.

As shown in FIG. 4, a first end 11 of the first handle 1 is a holding portion to be held by the doctor during operation. The second end 12 of the first handle 1 can be rotatably connected to a first end 21 of the second handle 2 through a first pin 14, the second end 22 of the second handle 2 is rotatably connected to the casing 54 of the stapler through a second pin 24. Further, a first torsion spring 15 sleeved on the first pin 14 is located between the first handle 1 and the second handle 2. A second torsion spring 25 sleeved on the second pin 24 is located between the second handle 2 and the casing 54 of the stapler. Therefore, when the slider 3 is in the first section of the slot 17, the stapler is in the insurance state, the first handle 1 can be rotated around the first pin 14 when pressed by the operator with a small holding force, and return to its initial position in a clockwise direction by the first torsion spring 15 when the external force is released. At this time, the second handle 2 is not rotated. When the slider 3 is in the second section of the slot 17, the second handle 2 can be actuated by the first handle 1, to rotate around the second pin 24, and return to its initial position by the second torsion spring 25 when the external force is released.

The handle assembly further includes a return spring for the slider. After the return spring is forced by the slider to be in a deformation state, during the process of the return spring returning from the deformation state to its initial state, the slider 3 is actuated to move from the second section to the first section of the slot 17. As shown in FIG. 4, in the embodiment, the return spring is a torsion spring 16, two ends of the torsion spring 16 are in contact with the slider 3 and the second handle 2, respectively. Therefore, when the slider 3 is moved from the first section to the second section of the slot 17, the slider 3 pushes the first end of the torsion spring 16 to generate deformation thereof. When the external force on the slider 3 is released, the slider 3 can be actuated by the returning force of the torsion spring 16, to return to the first section of the slot 17. In other embodiments, the return spring for the slider can also be an extension spring, a compression spring etc.

In the following, the structure of the slider of the embodiment is described combining FIGS. 5-9. A sliding portion 31 movably located in the slot 17 and a slider guiding portion 32 are provided on the slider, and a handle guiding portion 26 is provided on the second handle 2. The slider 3 is in the second section of the slot 17, and when the first handle 1 is pressed to rotate, the slider guiding portion 32 is in contact with the handle guiding portion 26.

In the embodiment, the first handle 1 includes a first cavity 13 having two side walls. Two slots 17 are provided on the two side walls of the first cavity 13, respectively. Correspondingly, the slider 3 includes two sliding portions 31 embedded in the two slots 17, respectively, and the sliding portions 31 are movable in the corresponding slots 17.

When the sliding portions 31 are located in the first sections of the slots 17, respectively, and the first handle 1 is pressed to rotate anticlockwise, the second handle 2 at least partially gets into the first cavity 13. Therefore, the second handle 2 cannot be moved by the first handle 1. When the sliding portions 31 are located in the second sections of the slots 17, respectively, and the first handle 1 is pressed to rotate anticlockwise, the slider guiding portion 32 is in contact with the handle guiding portion 26. Therefore, the second handle 2 can be moved along with the first handle 1, to fire the stapler.

Further, the second handle 2 may include a second cavity 23 including two side walls, the handle guiding portion 26 is located in the second cavity 23, and a width of the handle guiding portion 26 is less than or equal to that of the slider guiding portion 32. The width of the handle guiding portion 26 and the slider guiding portion 32 here mean the widths along a direction perpendicular to the side walls of the first cavity 13, which are not intended as a limitation on the scope of the present disclosure.

Further, the slider 3 may include a boss 33 located between one of the sliding portions 31 and the slider guiding portion 32. A concave portion 331 is provided on the top of the boss 33, and the return spring 16 for the slider as aforementioned is provided between an inner surface of the concave portion 331 and the second handle 2.

Figure 9:
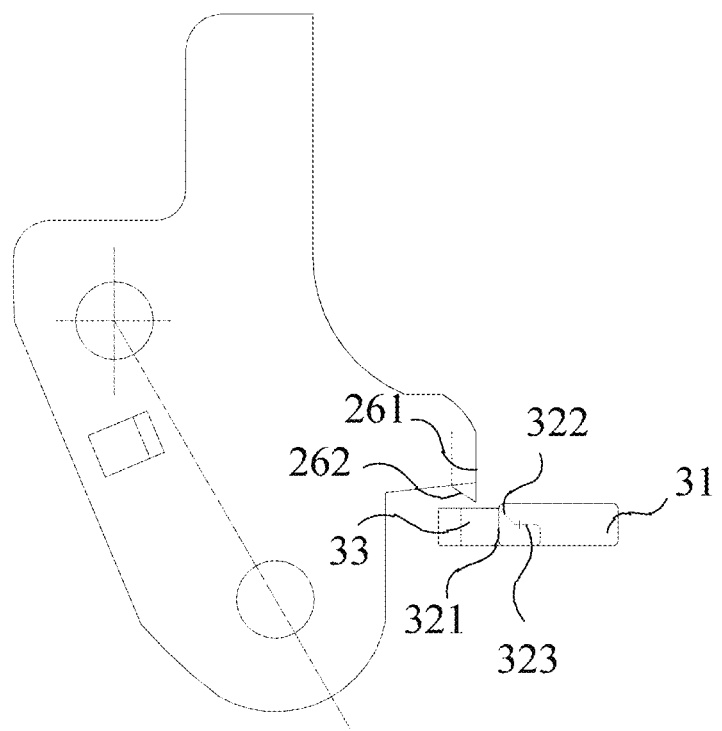
FIG. 9 is a schematic view of the second handle and the slider when the slider is in the first section of the slot, according to the embodiment of the present disclosure.

As shown in FIG. 9, the handle guiding portion 26 includes a first slider guiding surface 261 and a second slider handle guiding surface 262 adjacent to each other. The slider guiding portion 32 includes a guiding section, that is, the left portion having an inclined surface in the FIG. 9. The guiding section includes a first slider guiding surface 321 and a second slider guiding surface 322. When the slider guiding portion 32 is in contact with the handle guiding portion 26 under the force of the indicator, the positions of the second slider guiding surface 322 and the second handle guiding surface 262 are corresponding and parallel to each other. Here the positions being corresponding to each other, refers to that the projections of the second slider guiding surface 322 and the second handle guiding surface 262 in a moving direction along the slot 17 are at least partially overlapped when the slider 3 is in the second section of the slot 17 and the first handle 1 is rotated anticlockwise. At this time, the second slider guiding surface 322 is in contact with the second handle guiding surface 262, the second slider guiding surface 322 applies forces on the second handle guiding surface 262. With the mutual forces between them, the slider 3 has a further movement tendency towards the slot 17, thereby acquiring a more stable engagement between the slider 3 and the second handle 2, to push the second handle to move.

To avoid imprecise sections, that is, to prevent from the state that the slider guiding portion 32 and the handle guiding portion 26 are likely and actually not engaged with each other. A guiding mechanism by an inclined surface is further added in the embodiment. The second handle guiding surface 262 and a length direction of the slot 17 have an angle less than 90°. That is to say, the second handle guiding surface 262 is an inclined surface as shown in FIG. 9. When the second handle guiding surface 262 is in contact with the second slider guiding surface 322, the second handle guiding surface 262 can be guided to move relatively to the second slider guiding surface 322, to enlarge the contact surface between them. When the two guiding surfaces are in completely fit with each other, the contact surface is larger than that between two flat surfaces. Therefore, the actuation of the first handle to the second handle is more reliable and stable.

Further, a friction between the second handle guiding surface 262 and the second slider guiding surface 322 is not big enough to influence the sliding between the second handle guiding surface 262 and the second slider guiding surface 322. Therefore, when the second slider guiding surface 322 is in contact with the second handle guiding surface 262, and the first handle 1 is rotated anticlockwise, the second slider guiding surface 322 applies a force F on the second handle guiding surface 262, and the force F includes two components F1 and F2 perpendicular to each other. The component F1 is perpendicular to the second slider guiding surface, and F1×β<F2, wherein, β is a friction coefficient between the second slider guiding surface 322 and the second handle guiding surface 262.

In the embodiment, as the slider guiding portion 32 and the handle guiding portion 26 are in contacted with each other in the form of cuspidal point to cuspidal point, the probability of a point locking up to another point is so small and can be ignored. Therefore, when the slider guiding portion 32 and the handle guiding portion 26 are in contacted with each other, they will be either completely engaged with each other, or completely depart from each other.

Further, the slider guiding portion 32 includes a connecting section adjacent to the guiding section, the connecting portion is the section similar to a platform on the right side in FIG. 9. In other embodiments, the connecting section can also not be in the shape of a platform. The platform portion is used to strengthen the guiding section and connect the sliding portions 31 on the two sides thereof. The connecting section includes a third slider guiding surface 323, adjacent to the second slider guiding surface 322.

In the embodiment, the structure of the slider guiding portion 32, the structure of the handle guiding portion 26 and the angle between the two portions 32, 26 are considered as exemplary only. In other embodiments, other structures can also be chosen, such as the structure that the second slider guiding surface 322 and the second handle guiding surface 262 both extend parallel to the extension direction of the slot, which is also within the scope of the present disclosure.

Figure 10:
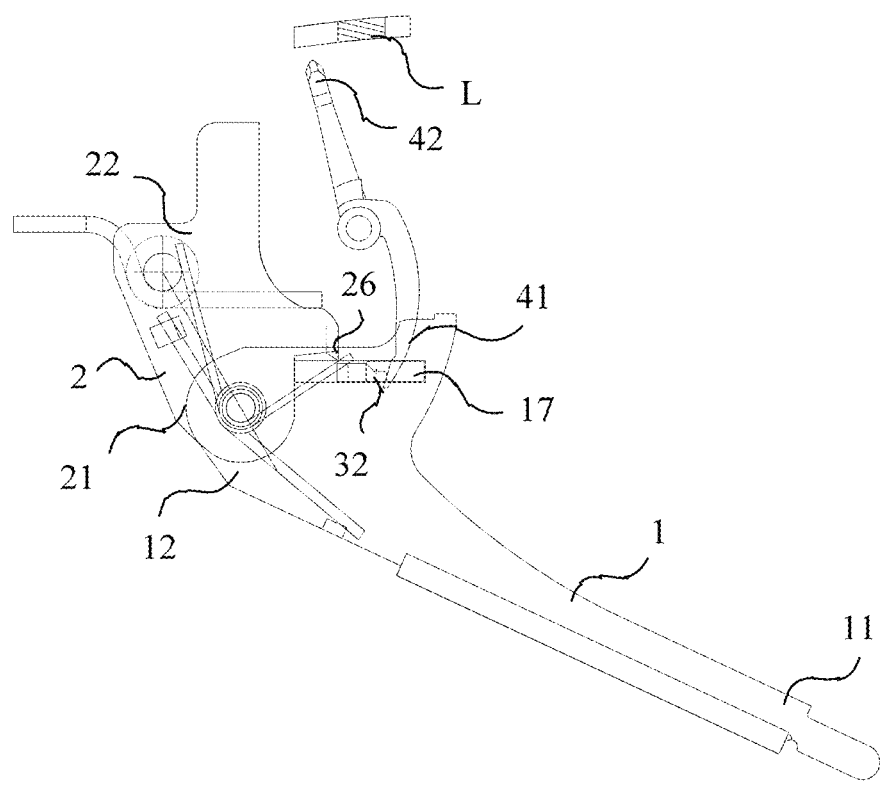
FIG. 10 is a schematic view of the handle assembly when the slider is in the first section of the slot and the first handle is not rotated, according to the embodiment of the present disclosure.
Figure 11:
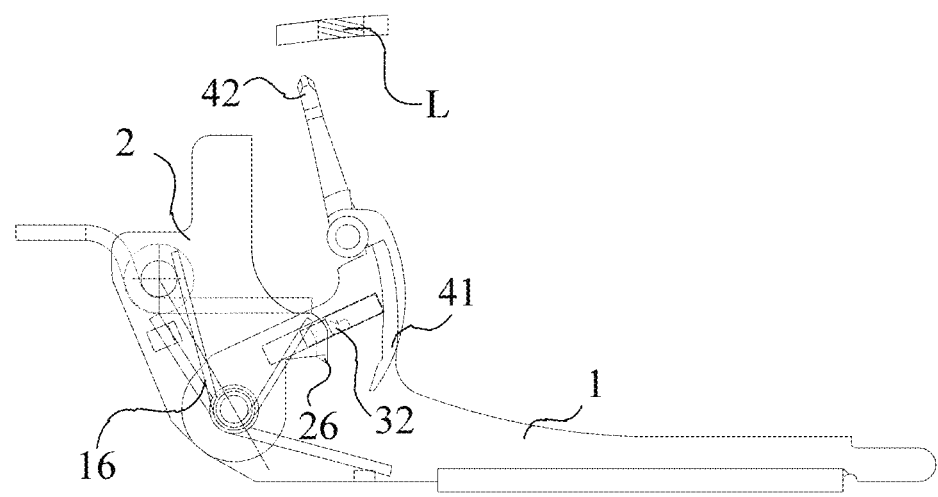
FIG. 11 is a schematic view of the handle assembly when the slider is in the first section of the slot and the first handle is rotated, according to the embodiment of the present disclosure.

In the following, FIGS. 9-11 are combined to describe the movement process of the first handle when the slider 3 is in the first section of the slot 17. In FIGS. 9-10, the first handle 1 is not rotated, while in FIG. 11, the first handle is rotated when pressed.

As shown in FIG. 10, the indicator 4 is fixed in the casing of the stapler through its fixed end. When the second end 42 of the indicator 4 is moved between the first and the second position areas, the first end 41 of the indicator 4 is also moved along. It should be noted that, the initial position of the slider 3 is an end of the first section far from the second section of the slider slot, that is, the right end of the slot in FIG. 10. In other embodiments, the first end 41 can also be used to limit the initial position of the slider 3. As shown in FIG. 10, when the knob is rotated, the second end 42 of the indicator 4 is pulled by the pulling sheet to be in the first position area, the first end of the indicator 4 gradually actuates the slider 3 to move from the first section towards the second section of the slot 17, however the slider 3 is not in the second section of the slot yet. The slider 3 is in the first section of the sliding slot 17, that is, the right section of the slot 17 in FIG. 10, and the first handle 1 is not rotated. FIG. 11 shows the state of the handle assembly after the first handle 1 is rotated. However, at this time, the handle guiding portion 26 is not in contact with the slider guiding portion 32, that is, the first handle 1 and the second handle 2 are not linked together through the slider 3. The second handle 2 will partially get into the first cavity 13, and the position of the second handle 2 is not changed, therefore, the pressing force applied on the first handle 1 by the operator is not transmitted to the second handle. The second handle 2 is still in its initial insurance position, and will not fire the stapler. As the torsion force of the first torsion spring is much less than the force required to fire the stapler, the doctor only need to overcome the torsion force of the first torsion spring 15. The doctor can still press the first handle 1 without actuating the second handle 2, thereby not firing the stapler. The doctor can also get the tactile feedback to know that the indicator 4 is not in the area indicating that the staple is ready to be fired, and the stapler is not fired.

Figure 12:
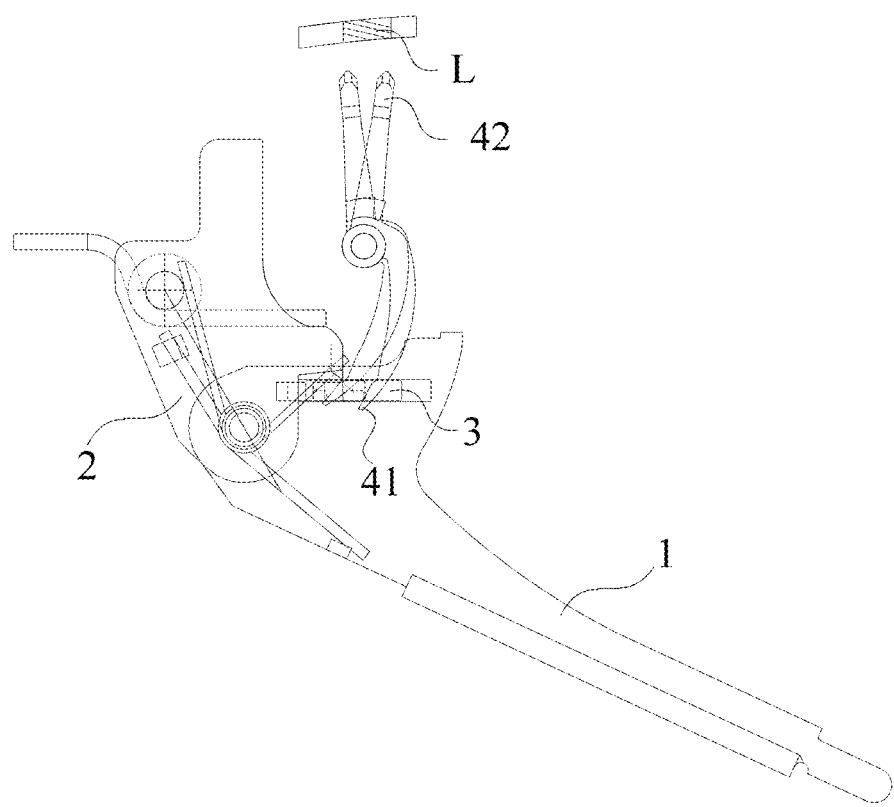
FIG. 12 is a schematic view of two different positions in the slot of the slider according to the embodiment of the present disclosure.
Figure 13:
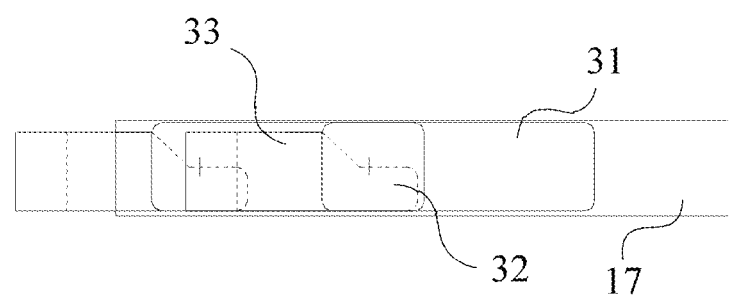
FIG. 13 is an enlarged view of the slot and the slider in FIG. 12.

In the following, FIGS. 12-21 are combined to describe the movement process of the first handle when the slider 3 is in the second section of the slot 17. Wherein, FIGS. 12 and 13 show two different positions of the slider 3 in the second section of the slot 17.

In the embodiment, there are two situations of the slider 3 when in the second section of the slot 17 (that is, the left section of the slot 17): one is the slider 3 being at a closer position of the second section of the slot 17, that is, the slider on the right side in FIG. 13, in which there is still a certain distance between the sliding portion 31 and the end surface of the second end of the slot 17; another is the slider 3 being at farther position of the second section of the slot 17, that is, the slider on the left side in FIG. 13, in which the sliding portion is basically in completely fit with the end surface of the second end of the slot 17. In the embodiment, the two situations both can realize the linkage of the first handle 1 and the second handle 2, therefore enlarging the operation area to fire the staple for the doctor, making the firing process more stable and decreasing the operation difficulty for the doctor. The structure is described here as exemplary only, in other embodiments, the left end surface can be indented towards the right side and only the first situation exists, which is within the scope of the present disclosure.

Figure 14:
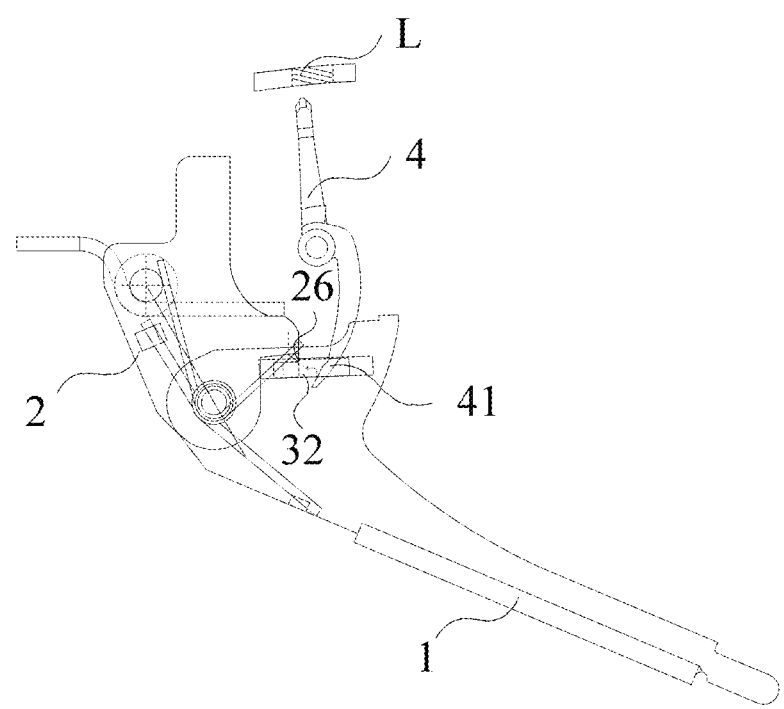
FIG. 14 is a schematic view of the handle assembly when the slider is at a closer position in the second section of the slot and the first handle is not rotated, according to the embodiment of the present disclosure.
Figure 15:
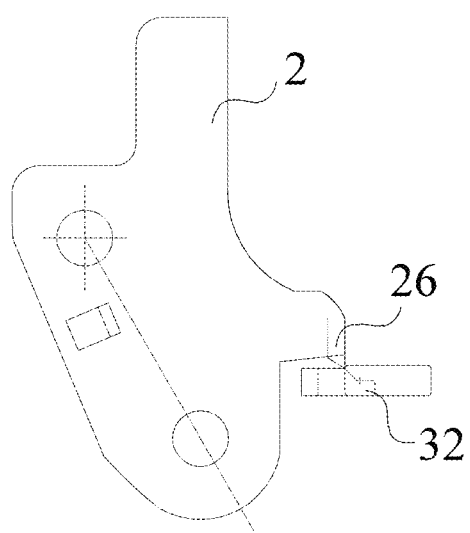
FIG. 15 is a schematic view of the second handle and the slider in FIG. 14.
Figure 16:
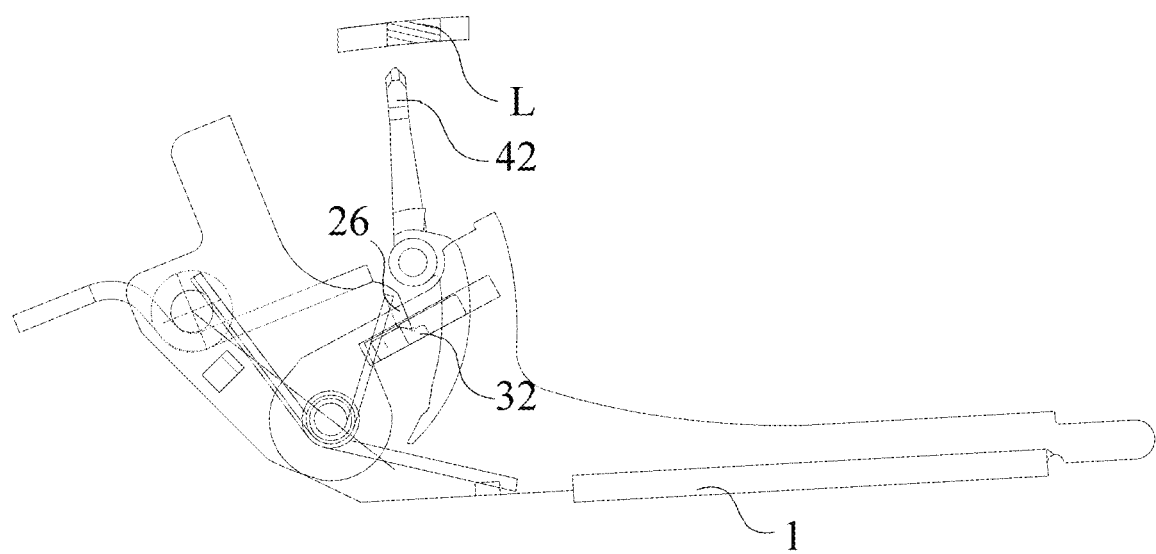
FIG. 16 is a schematic view of the handle assembly when the slider is at the closer position in the second section of the slot and the first handle is rotated, according to the embodiment of the present disclosure.

As shown in FIG. 14, the indicator 4 is rotated by the pulling sheet, the second end 42 of the indicator 4 just gets into the second position area L, the slider 3 is at the closer position of the second section of the slot 17, and the first handle 1 is not rotated. At this time, if the knob continues to be rotated, the pulling sheet continues to actuate the first end 41 of the indicator 4 to push the slider 3 to move towards the left side along the slot 17, correspondingly, the distance between the anvil and the cartridge is shortened. Along with that, as shown in FIG. 15, the overlap area between the projections of the slider guiding portion 32 and the handle guiding portion 26 along the moving direction along the slot 17 are gradually increased, thereby acquiring a more reliable connection between the first handle 1 and the second handle 2. As shown in FIG. 16, the first handle 1 and the second handle 2 are linked together through the slider 3. When the first handle 1 is pressed, the rotation of the first handle 1 actuates the second handle 2 to move from the insurance position to the firing position. The second end of the second handle 2 will be in contact with the firing block 55 of the stapler, to fire the stapler. During the firing process, the second end of the first handle 1 is in contact with the pulling sheet when rotated, and lift the pulling sheet to depart from the indicator 4, the indicator 4 is returned to its initial position by the indicator return mechanism.

Figure 17:
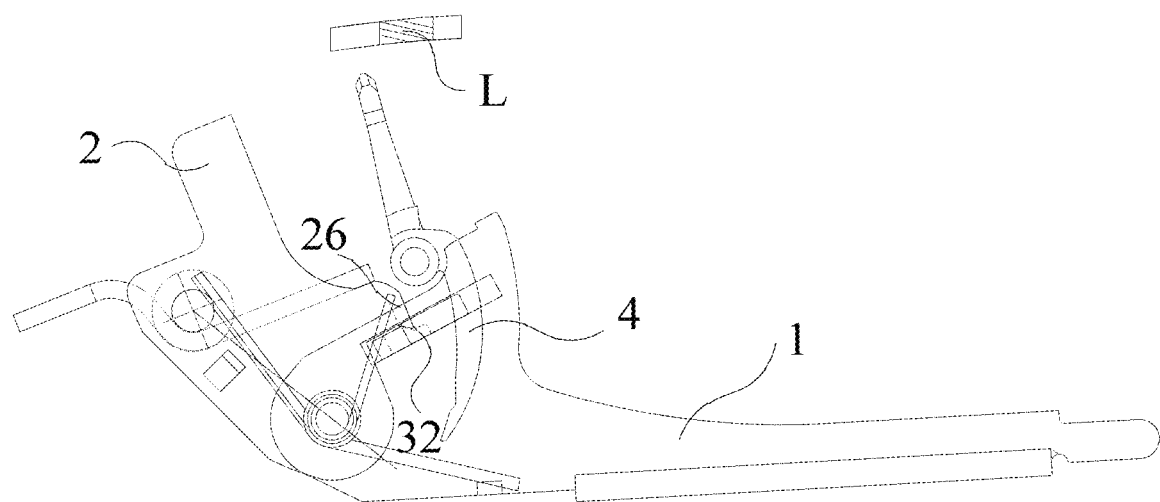
FIG. 17 is a schematic view of the handle assembly when the slider is at the closer position in the second section of the slot and an indicator is returned to its initial position, according to the embodiment of the present disclosure.

FIG. 17 shows the structure of the handle assembly when the first handle 1 is not returned with the operator keep holding it, while the indicator is returned, after the stapler is fired. At this time, the second end 42 of the indicator 4 is returned the first position area, and the slider 3 is still not returned yet, for the slider guiding portion 32 being limited by the handle guiding portion 26. At this time, if the first handle 1 is released, the first handle 1 will return to its initial position, the slider 3 can return to the first section of the slot 17 by the return torsion spring 16, and the second handle is returned to the insurance position clockwise under the restoring force of the second torsion spring 25.

Figure 18:
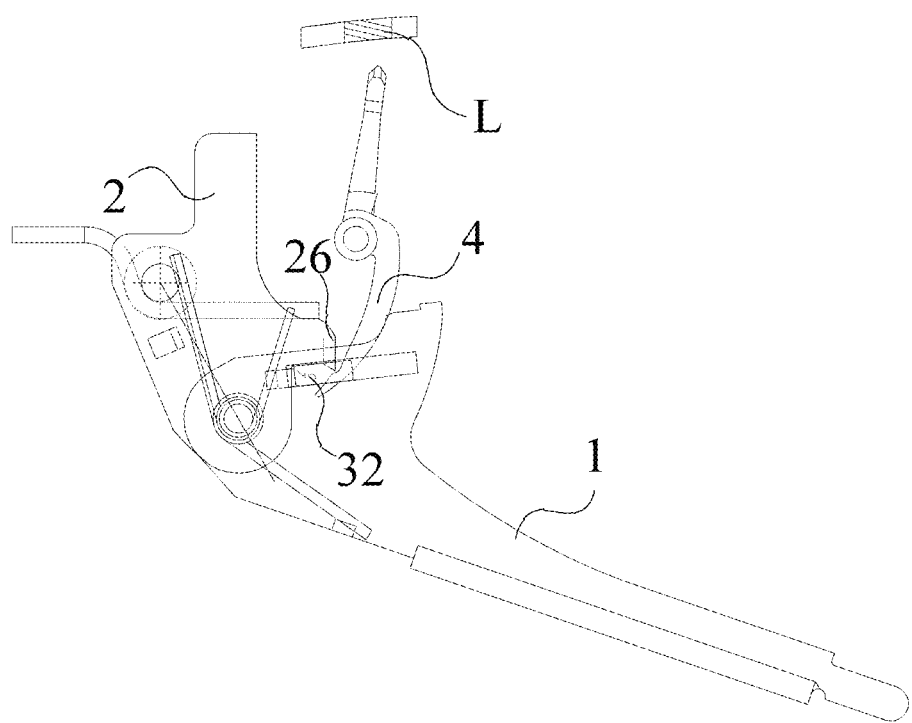
FIG. 18 is a schematic view of the handle assembly when the slider is at a farther position in the second section of the slot and the first handle is not rotated, according to the embodiment of the present disclosure.
Figure 19:
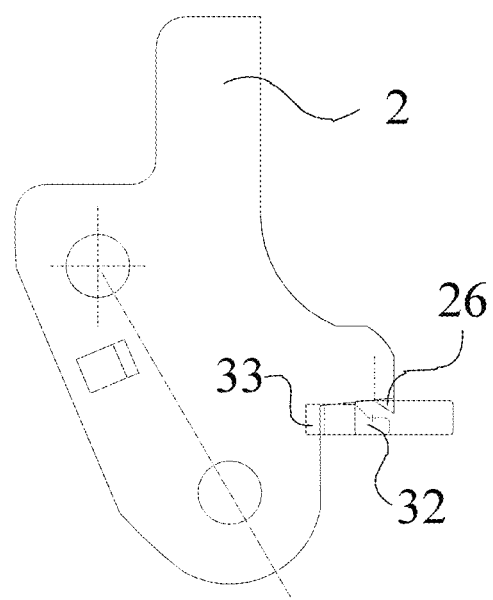
FIG. 19 is a schematic view of the second handle and the slider in FIG. 18.

As shown in FIG. 18, the slider is at the farther position of the second section of the slot 17, and the first handle 1 is not rotated. The second end 42 of the indicator 4 gets into the second position area L, and the position of the second end 42 of the indicator 4 in FIG. 18 is on the right side of that in FIG. 14, and the position of the first end 41 of the indicator 4 in FIG. 18 is on the left side of that in FIG. 14, thereby pushing the slider 3 closer to the end surface of the second section of the slot 17. As shown in FIG. 19, the overlap area between the projections of the slider guiding portion 32 and the handle guiding portion 26 in the moving direction along the slot 17 are larger, and the connection between the first handle 1 and the second handle 2 is more reliable.

Figure 20:
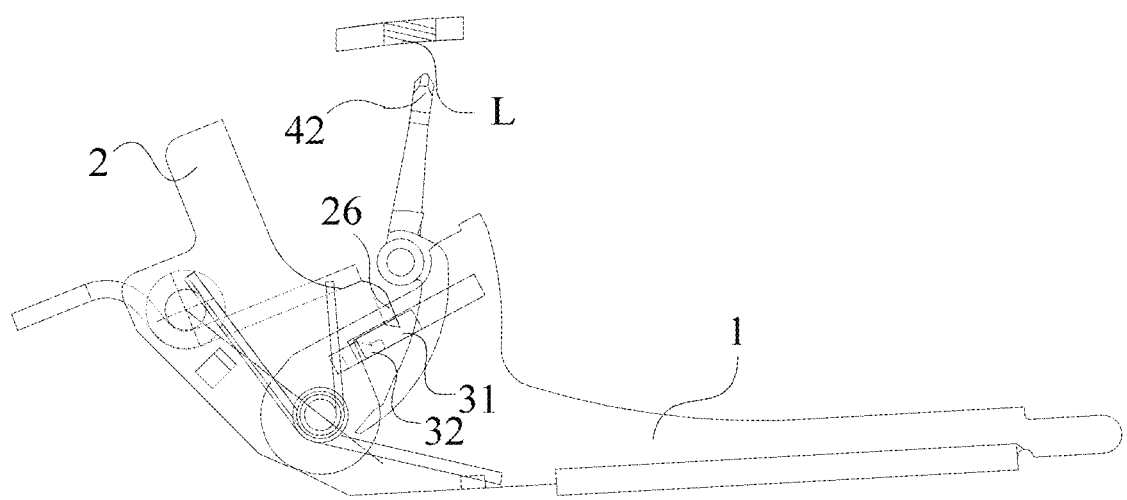
FIG. 20 is a schematic view of the handle assembly when the slider is at the farther position in the second section of the slot and the first handle is rotated, according to the embodiment of the present disclosure.

As shown in FIG. 20, when the first handle 1 is rotated, the second handle 2 is actuated by the first handle 1 for the linkage between them through the slider 3, to move from the insurance position to the firing position. The second end of the second handle 2 will be in contact with the firing block 55 of the stapler, to fire the stapler.

Figure 21:
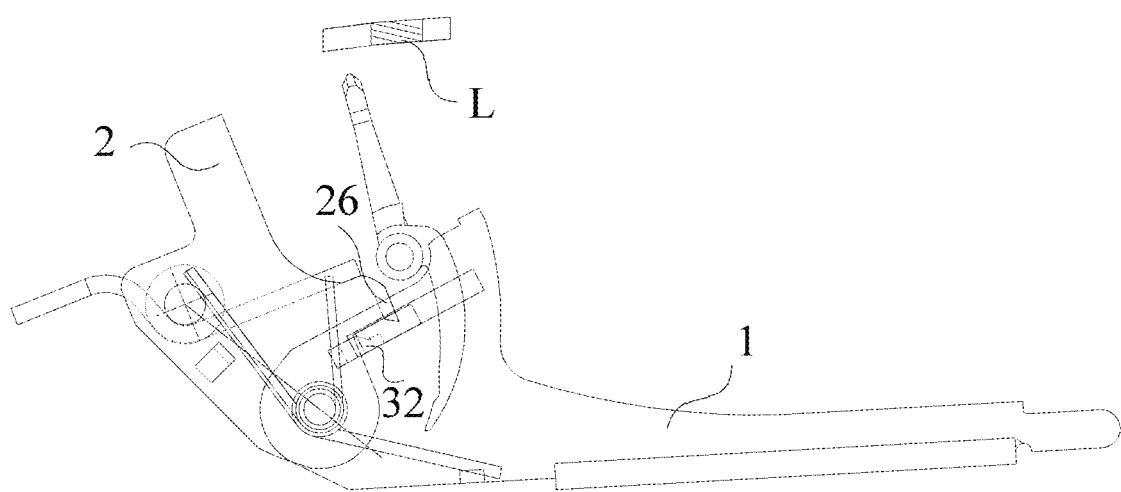
FIG. 21 is a schematic view of the handle assembly when the slider is at the farther position in the second section of the slot and the indicator is returned to its initial position, according to the embodiment of the present disclosure.

FIG. 21 shows the structure of the handle assembly when the first handle 1 is not returned while the indicator is returned, after the stapler is fired. The process is the same with that when the indicator 4 just gets into the green area, and repeated description will be omitted here.

The present disclosure further provides a stapler, including the handle assembly. When the stapler is not ready to be fired, the second handle cannot be actuated by the first handle, and the stapler won't be fired. The doctor can also judge whether the stapler is ready to be fired or not according to his operation experience. The second handle can only be actuated by the first handle when the stapler is ready to be fired, to fire the staple. Therefore, the stapler is prevented from being fired by mistake, and the casing of the stapler is prevented from being cracked at the same time.

The handle assembly and the stapler including the same has the following advantages.

In the present disclosure, the handle assembly includes a first handle and a second handle, and only the movement of the second handle can fire the stapler to cut and suture tissues; during operation, the first handle can be pressed by the doctor to move no matter whether the stapler is ready to be fired or not, while, the stapler cannot be fired by the first handle through the second handle when the stapler is not ready to be fired. The doctor can judge whether the stapler is ready to be fired or not according to his operation experience. The stapler can only be fired by the first handle through the second handle when the stapler is ready to be fired. The casing can be prevented from being cracked by pressing the handle vigorously, and the operators' experience is improved.

The above is a detailed description of the present disclosure in connection with the specific preferred embodiments, and the specific embodiments of the present disclosure are not limited to the description. Modifications and substitutions can be made without departing from the spirit and scope of the present disclosure.

What is claimed is:

1. A handle assembly for firing a stapler, comprising:
   an indicator, movable between a first position area and a second position area;
   a first handle and a second handle;
   a slot, provided in the first handle and comprising a first section and a second section connected with each other;
   a slider, slidably located in the slot;
   wherein, when the indicator is moved from the first position area to the second position area, the slider is actuated to move from the first section to the second section of the slot;
   when the slider is in the first section of the slot, and the first handle is rotated in a first direction, the slider is not in contact with the second handle, therefore, the second handle is in an insurance position;
   when the slider is in the second section of the slot, and the first handle is rotated in the first direction, the slider is in contact with the second handle and actuates the second handle to move from the insurance position to a firing position.

2. The handle assembly according to claim 1, wherein, the indicator is connected to a distal end of a pulling sheet, a proximal end of the pulling sheet is sleeved on a screw rod having a proximal end connected to a knob, when the knob is rotated to pull the pulling sheet to move towards the proximal end thereof, the indicator is moved by the pulling sheet from the first position area to the second position area.

3. The handle assembly according to claim 1, wherein, the first handle is rotatably connected to the second handle through a first pin, the second handle is rotatably connected to a casing of the stapler through a second pin.

4. The handle assembly according to claim 3, wherein, a first torsion spring and a second torsion spring are sleeved on the first pin and the second pin, respectively, two ends of the first torsion spring are in contact with the first handle and the second handle, respectively, two ends of the second torsion spring are in contact with the second handle and the casing of the stapler, respectively.

5. The handle assembly according to claim 1, further comprising a return spring for the slider, after the return spring is forced by the slider to be in a deformation state, the return spring restores from the deformation state to its initial state, thereby actuating the slider to move from the second section to the first section of the slot.

6. The handle assembly according to claim 5, wherein, the return spring is a return torsion spring, two ends of the return torsion spring are in contact with the slider and the second handle, respectively.

7. The handle assembly according to claim 1, wherein, the second handle comprises a handle guiding portion, the slider comprises a sliding portion movably located in the slot and a slider guiding portion;
   when the slider is in the second section of the slot, and the first handle is rotated in a first direction, the slider guiding portion is in contact with the handle guiding portion.

8. The handle assembly according to claim 7, wherein, the handle guiding portion comprises a first handle guiding surface and a second handle guiding surface adjacent to each other, the slider guiding portion comprises a guiding section having a first slider guiding surface and a second slider guiding surface adjacent to each other; when the slider guiding portion is in contact with the handle guiding portion, the positions of the second slider guiding surface and the second handle guiding surface are in corresponding and parallel to each other.

9. The handle assembly according to claim 8, wherein, an angle between the second handle guiding surface and a length direction of the slot is less than 90°.

10. The handle assembly according to claim 9, wherein, when the second slider guiding surface is in contact with the second handle guiding surface, and when the first handle is rotated in the first direction, a force F is applied to the second handle guiding surface by the second slider guiding surface, the force F comprises two components F1 and F2 perpendicular to each other, the component F1 is perpendicular to the second slider guiding surface, and $F1 \times \beta < F2$, wherein, $\beta$ is a friction coefficient between the second slider guiding surface and the second handle guiding surface.

11. The handle assembly according to claim 9, wherein, the slider guiding portion further comprises a connecting section adjacent to the guiding section, the connecting section comprises a third slider guiding surface adjacent to the second slider guiding surface.

12. The handle assembly according to claim 7, wherein, the first handle comprises a first cavity having two side walls, two slots are provided on the two side walls of the first cavity, respectively, the slider comprises two sliding portions and the slider guiding portion, the two sliding portions are movably located in the slot;

when the two sliding portions are in the first sections of the two slots, respectively, and the first handle is rotated in the first direction, the second handle at least partially gets into the first cavity;

when the sliding portions are in the second sections of the two slots, respectively, and the first handle is rotated in the first direction, the slider guiding portion is in contact with the second handle to prevent the second handle from continuing to get into the first cavity.

13. The handle assembly according to claim 12, wherein, the second handle comprises a second cavity having two side walls, the handle guiding portion is in the second cavity, and a width of the handle guiding portion is less than or equal to that of the slider guiding portion.

14. The handle assembly according to claim 12, wherein, the slider further comprises a boss located between one of the sliding portions and the slider guiding portion, a concave portion is provided on the top of the boss, and a return spring for the slider is provided between an inner surface of the concave portion and the second handle.

15. A stapler, comprising the handle assembly according to claim 1.

* * * * *